United States Patent
Malaczynski et al.

(10) Patent No.: US 10,329,987 B2
(45) Date of Patent: Jun. 25, 2019

(54) PARTICULATE MATTER SENSOR SIGNAL CORRECTION

(71) Applicant: DELPHI TECHNOLOGIES IP LIMITED, St. Michael (BB)

(72) Inventors: Gerard W. Malaczynski, Bloomfield Hills, MI (US); Gregory T. Roth, Davison, MI (US)

(73) Assignee: DELPHI TECHNOLOGIES IP LIMITED (BB)

( * ) Notice: Subject to any disclaimer, the term of this patent is extended or adjusted under 35 U.S.C. 154(b) by 257 days.

(21) Appl. No.: 15/265,994

(22) Filed: Sep. 15, 2016

(65) Prior Publication Data

US 2018/0073415 A1 Mar. 15, 2018

(51) Int. Cl.
*G01N 15/00* (2006.01)
*G01M 15/10* (2006.01)
*G01N 15/06* (2006.01)
*F01N 11/00* (2006.01)

(52) U.S. Cl.
CPC ......... *F01N 11/007* (2013.01); *G01M 15/102* (2013.01); *G01N 15/0606* (2013.01); *G01N 15/0656* (2013.01); *F01N 2560/05* (2013.01); *G01N 2015/0046* (2013.01)

(58) Field of Classification Search
CPC .......................... G01N 15/0656; F01N 11/007
USPC ....................................................... 73/23.31
See application file for complete search history.

(56) References Cited

U.S. PATENT DOCUMENTS

| | | |
|---|---|---|
| 5,049,255 A | 9/1991 | Wolfe et al. |
| 6,321,531 B1 | 11/2001 | Caren et al. |
| 8,677,803 B2 | 3/2014 | Hocken et al. |
| 8,823,401 B2 | 9/2014 | Roth et al. |
| 2008/0000221 A1 | 1/2008 | Silvis |
| 2009/0230962 A1 | 9/2009 | White et al. |
| 2009/0301058 A1 | 12/2009 | Boehler et al. |

(Continued)

FOREIGN PATENT DOCUMENTS

DE 102011086148 A1 5/2013

OTHER PUBLICATIONS

SAE International, 2012-01-0372, published Apr. 16, 2012, "Sensing of Particulate Matter for On-Board Diagnosis of Particulate Filters", Harry Husted, Gregory Roth, Scott Nelson, Lary Hocken, Gary Fulks, David Racine; Delphi Automotive Systems, LLC.

*Primary Examiner* — John Fitzgerald
*Assistant Examiner* — Rodney T Frank
(74) *Attorney, Agent, or Firm* — Joshua M. Haines

(57) ABSTRACT

A system includes an exhaust system fluidly configured to define an exhaust stream. A sensor is arranged in the exhaust system and is configured to be exposed to the exhaust stream and accumulate particulate matter on the sensor. The sensor provides a signal that varies based upon an amount of particulate matter on the sensor. A control system is in communication with the sensor. The control system includes a controller configured to calculate a differential of a conductance signal related to the signal, compare consecutive differentials to identify an erroneous differential in an abnormal signal based upon an anomaly relating to the accumulation of the particulate matter, and reconstruct the abnormal signal by correcting the erroneous differential to produce a corrected, decimated conductance signal. The control system is configured to determine a total accumulated particulate matter adjusted for the anomaly.

20 Claims, 6 Drawing Sheets

(56) References Cited

U.S. PATENT DOCUMENTS

| | | |
|---|---|---|
| 2013/0233051 A1 | 9/2013 | Harshbarger et al. |
| 2014/0345362 A1 | 11/2014 | Lee et al. |
| 2015/0114339 A1 | 4/2015 | Sellnau et al. |
| 2015/0211429 A1 | 7/2015 | Hocken et al. |
| 2016/0131013 A1 | 5/2016 | Yi et al. |
| 2016/0201537 A1 | 7/2016 | Ettireddy et al. |
| 2016/0265413 A1 | 9/2016 | Willimowski et al. |
| 2017/0037754 A1 | 2/2017 | Shade et al. |
| 2017/0067813 A1 | 3/2017 | Zhang |

PARTICULATE MATTER SENSOR SIGNAL CORRECTION

BACKGROUND

This disclosure relates to a system and method of correcting a particulate matter sensor signal for soot deposit stochastic variation in the form of large particle strikes, blow-offs, and periodic delaminations.

Rich combustion conditions, such as those which occur in diffusion flame processes that are present in diesel engines and other internal combustion engines, produce particulate matter, which is carried in its exhaust stream. Particulate matter emissions are typically limited by emissions regulations and it is common for modern diesel engines to be equipped with a particulate filter. As part of the emissions regulations, diagnosis of the particulate filter is mandated and the use of a particulate matter sensor is one such diagnostic system. Thus, it is desirable to accurately measure particulate matter real-time in vehicles to ensure that the engine and particulate filter are operating in compliance with government regulations. It is also desirable to measure particulate matter using emissions testing equipment during engine development on a dynamometer, for example.

One type of particulate matter sensor includes electrodes that are closely spaced on an electrically non-conductive substrate. As particulate matter accumulates between the electrodes, the sensor's electric resistance decreases as the initially non-conductive substrate surface between electrodes becomes gradually more electrically conductive due to the deposited soot, which is indicative of the amount of particulate matter in the sensed exhaust pipe, either directly produced by the combustion process or its remnants escaping the action of the particulate filter.

Experimentally observed step-like unusual changes in the measured particulate matter deposit resistance are commonly attributed to either occasional bombardment of the sensor surface with particles much larger than the typical size within the particles' size distribution, or losses of already-deposited particle mass due to blow-offs. This dramatic alteration of particulate matter resistance gradient measured in the time domain corrupts the particulate matter assessment algorithms which may be based on the measure of the cycle time, i.e., time markers representing arbitrarily selected sensor resistances indicating the start of sensing cycle and its end. These error effects are explained in, for example, "Sensing of Particulate Matter for On-Board Diagnosis of Particulate Filters", H. Husted et al, SAE Int. J. Engines 5(2) (2012).

There is a need to account for the contribution of large particle strikes and/or blow-offs, which corrupt the signal and provide an inaccurate particulate matter reading.

SUMMARY

In one exemplary embodiment, a method of estimating particulate matter in an exhaust stream includes the steps of accumulating particulate matter on a sensor. The sensor provides a signal that varies based upon an amount of particulate matter on the sensor. A differential of a conductance signal related to the signal is calculated. Consecutive differentials are compared to identify an erroneous differential in an abnormal signal based upon an anomaly relating to the accumulation of the particulate matter. The abnormal signal is reconstructed by correcting the erroneous differential to produce a corrected, decimated conductance signal.

In a further embodiment of the above, the signal is an electric resistance signal with the anomaly and has an irregular signal shape. The conductance signal has a generally parabolic shape with the anomalies inducing well-behaved step changes.

In a further embodiment of any of the above, the calculating step includes generating a first differential signal from the conductance signal to provide a generally linear signal.

In a further embodiment of any of the above, the calculating step is performed at a first sampling frequency. The reconstructing step is performed at a second sampling frequency that is lower than the first sampling frequency.

In a further embodiment of any of the above, the reconstructing step includes conforming the erroneous differential to the generally linear signal, which provides a decimated conductance signal that is generally linear.

In a further embodiment of any of the above, the method includes a step of determining a total accumulated particulate matter, adjusted for the anomaly. The anomaly corresponds to a large particle strike condition on the sensor. The large particle strike condition causes a sudden increase in the conductance signal. The reconstructing step includes decreasing the erroneous differential to a level represented by a previous, not questionable or already corrected element, or mean or median of previous elements in the measurement sample array, or an earlier array if the questionable sample is the first element in a currently processed array.

In a further embodiment of any of the above, the total accumulated particulate matter determining step is performed subsequent to the reconstructing step and includes adding in a compensation for the erroneous differential created by large particles, thus retaining the fidelity of the determining step by including the mass of the large particle.

In a further embodiment of any of the above, the method includes a step of determining a total accumulated particulate matter adjusted for the anomaly. The anomaly corresponds to a particulate blow-off condition on the sensor causing a sudden decrease in the conductance signal. The reconstructing step includes increasing the erroneous differential to a level represented by a previous, not questionable or already corrected element, or mean or median of previous elements in the measurement sample array, or earlier array if the questionable sample is the first element in a currently processed array.

In a further embodiment of any of the above, the method includes a step of representing a system-specific electronic noise defining a minimum blow-off detection level which would cause rejection of noise-driven conductance signal and an undesired differential correction. The reconstructing step is performed above the minimum blow-off detection level.

In a further embodiment of any of the above, individual arrays of the first sampling frequency include a first sample point which represents the last sampling point from a previous array. The second sampling frequency includes decimated samples from a corrected array.

In a further embodiment of any of the above, the first sampling frequency is multiple times the second sampling frequency.

In a further embodiment of any of the above, the method includes a step of performing a measurement cycle that includes a deadband zone, followed by an active zone, which is followed by a regeneration zone. The accumulating, calculating, comparing and reconstructing steps are performed during the deadband and active zone.

In a further embodiment of any of the above, an exhaust system is fluidly connected to an engine. The exhaust system defines the exhaust stream. The sensor includes a heater and is provided in the exhaust system and energizes the heater in the regeneration zone.

In a further embodiment of any of the above, the method includes a step of initiating a regeneration of the sensor once the total accumulated particulate matter reaches a predetermined threshold based on the corrected conductance signal.

In a further embodiment of any of the above, the method includes a step of initiating a regeneration of the sensor prior to the total accumulated particulate matter reaching a predetermined threshold if an unstable soot deposit condition is identified.

In a further embodiment of any of the above, the anomaly corresponds to the unstable soot deposit condition on the sensor. The unstable condition corresponds to sudden increases and decreases in the conductance signal in a repeating pattern.

In another exemplary embodiment, a system includes an exhaust system fluidly configured to define an exhaust stream. A sensor is arranged in the exhaust system and configured to be exposed to the exhaust stream and accumulate particulate matter on the sensor. The sensor provides a signal that varies based upon an amount of the particulate matter on the sensor. A control system is in communication with the sensor. The control system includes a controller configured to calculate a differential of a conductance signal related to the signal, compare consecutive differentials to identify an erroneous differential in an abnormal signal based upon an anomaly relating to the accumulation of the particulate matter, and reconstruct the abnormal signal by correcting the erroneous differential to produce a corrected, decimated conductance signal. The control system is configured to determine a total accumulated particulate matter adjusted for the anomaly.

In a further embodiment of any of the above, the sensor includes a heater. The controller is configured to energize the heater based upon the total accumulated particulate matter.

In a further embodiment of any of the above, the control system performs a sensing cycle that includes a deadband zone, followed by an active zone, which is followed by a regeneration zone. The controller is configured to determine the total accumulated particulate matter during the active zone.

In a further embodiment of any of the above, the control system outputs particulate matter data continuously during vehicle operation or during an engine test procedure.

BRIEF DESCRIPTION OF THE DRAWINGS

The disclosure can be further understood by reference to the following detailed description when considered in connection with the accompanying drawings wherein.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

Figure 1:
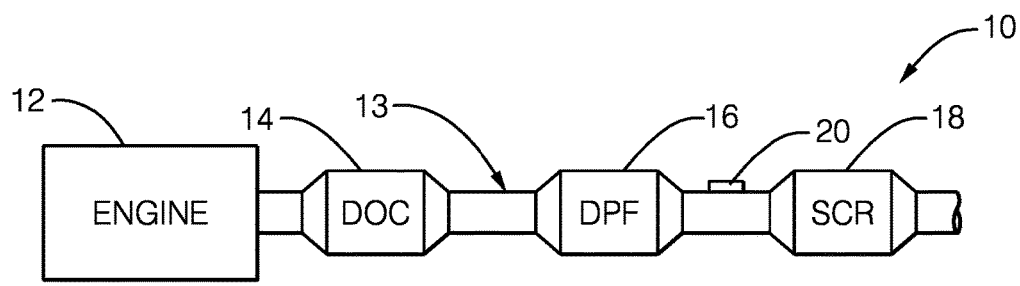
FIG. 1 is a schematic view of an exemplary powertrain system.

An example vehicle powertrain system 10 is shown in FIG. 1. The system 10 includes an engine 12, which in this non-limiting exemplary embodiment is a diesel engine, fluidly connected to an exhaust system 13 that includes a diesel oxidation catalyst (DOC) 14 and a diesel particulate filter (DPF) 16. A selective catalyst reduction (SCR) catalyst, such as those used in conjunction with a urea injection system, is arranged downstream from the DPF 16.

A particulate matter (PM, also referred to as "soot") sensor 20 is arranged in the exhaust system 13, typically in proximity to the DPF 16, although it should be understood that the PM sensor 20 may be located elsewhere. The PM sensor 20 is configured to be exposed to the exhaust stream and accumulate PM on its internal sensing element. The PM sensor 20 provides a resistance signal that varies based upon an amount of the PM on the sensor.

Figure 2:
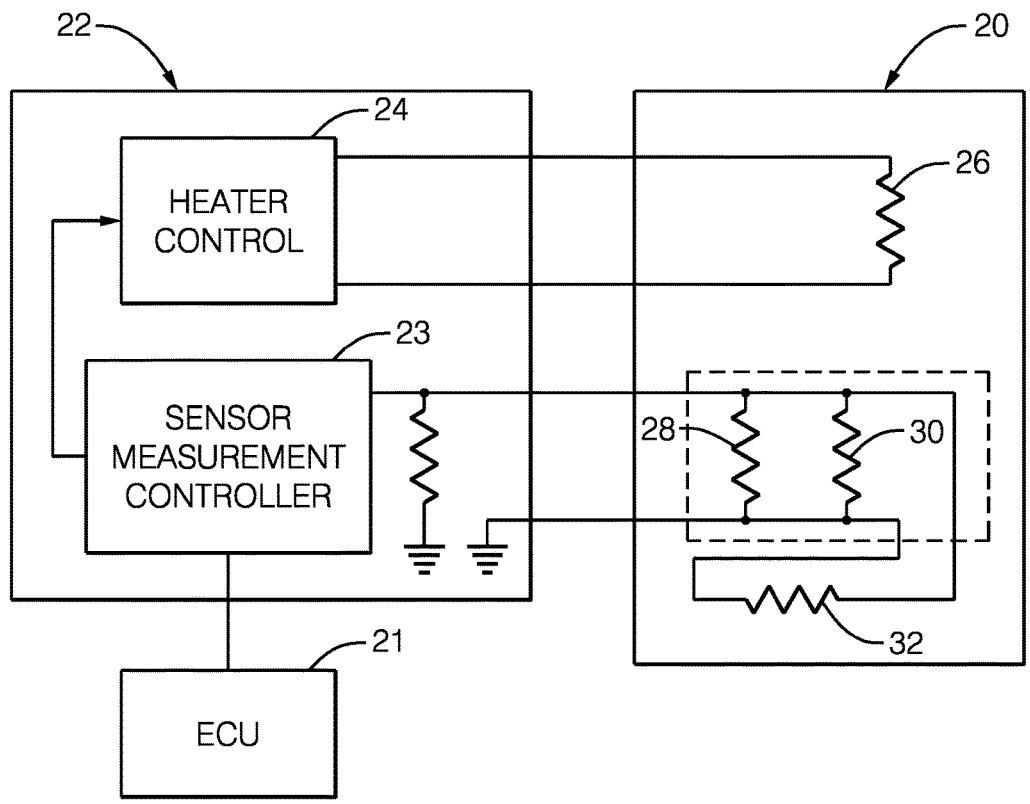
FIG. 2 is a circuit schematic for a particulate matter sensor and its controller.
Figure 3:
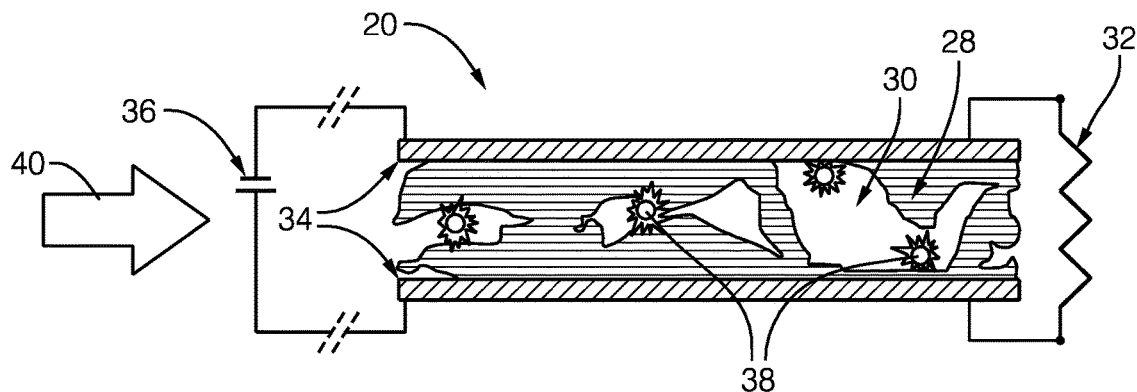
FIG. 3 is schematic of the particulate matter sensor during a particulate matter particle strike.

Referring to FIG. 2, a control system 21, such as an engine control unit (ECU), is in communication with the PM sensor controller 22 which includes a sensor measurement controller 23 that controls a sensing cycle (e.g., shown in FIGS. 4A and 4B) for the sensor based upon its resistance. In one type of PM sensor 20, soot, substrate and bias resistor 28, 30, 32 are connected in parallel with one another. The substrate resistor 30 represents the resistance of a "clean", i.e. not contaminated with the soot deposit, sensor 20, and the bias resistor 32 is used for diagnosing the sensor 20. The substrate resistance is very large relative to the other resistances. The soot-representing resistor 28 is provided by a pair of spaced apart electrodes 34 such that when no PM is present, the electrodes provide an open circuit in parallel with bias resistor 32 and substrate resistance 30 with a power source 36, as shown in FIG. 3. As PM 38 in the exhaust stream 40 deposits on the sensor surface between electrodes 34 the soot deposit resistance in parallel with the bias resistor provide gradually decreasing effective electrical resistance (or increasing effective electrical conductance) of the sensor measured by the system electronics.

After a predetermined sensor electrical conductance is reached, which represents a maximum desired soot accumulation at the sensor surface, there is a need for the removal of the soot as further soot accumulation might lead to a poor reliability of the data interpretation and carry a risk of ineffective soot oxidation (cleaning) procedure with the heater 26 integrated with the sensor. Returning to FIG. 2, to begin the sensing cycle again, the sensor measurement controller 23 commands a heater module 24 to activate a sensor heater 26 in the PM sensor 20, which oxidizes the accumulated PM and regenerates the sensor, typically in response to a threshold total accumulated particulate matter being reached.

The PM sensor controller 22 can be part of an onboard vehicle PM sensing system or part of an emissions testing system suitable for use in, for example, a test laboratory during engine testing and calibration. In the example of an emissions test system, the PM sensor controller 22 may output particulate matter data to a laboratory data acquisition system during the engine test procedure.

Figure 4A:
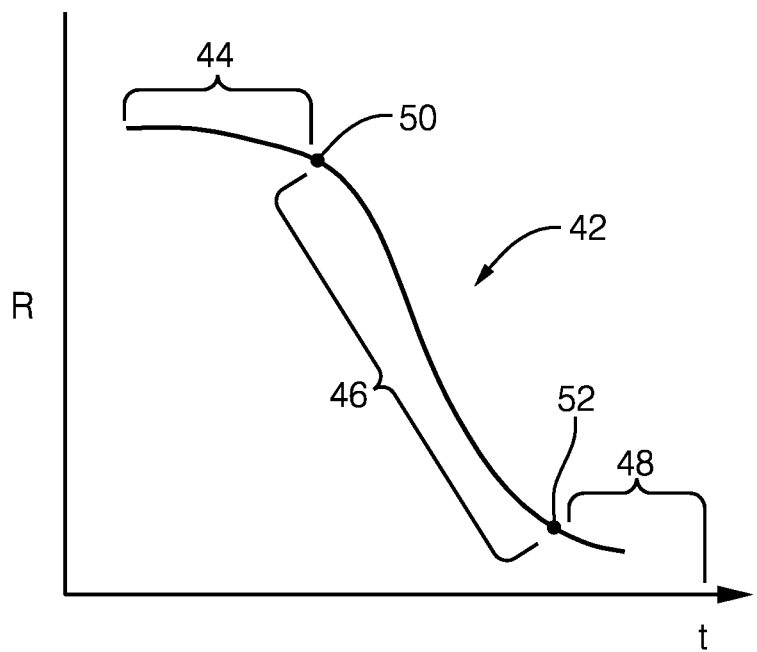
FIG. 4A is a graph of a sensing cycle based upon resistance versus time.
Figure 4B:
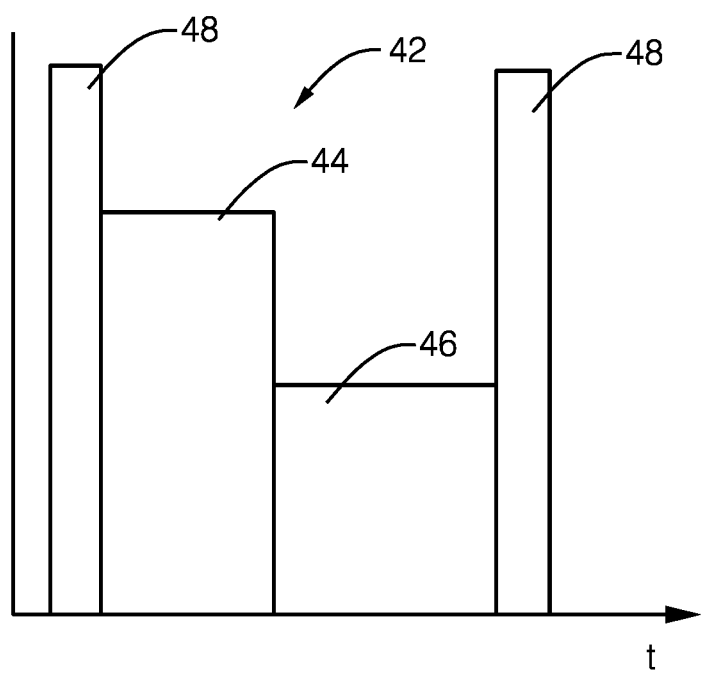
FIG. 4B is a schematic illustrating various zones during the sensing cycle.

One example sensing cycle 42 is shown in FIGS. 4A and 4B. Referring to FIG. 4B, the sensing cycle 42 has a deadband zone 44, an active zone 46 and a regeneration zone 48. As shown in FIG. 4A, prior to the starting point 50 of the active zone 46, the resistance of the sensor 20 is relatively flat and unchanged since sufficient PM has not yet accumulated in the sensor 20 to bridge the electrodes 34. From the starting point 50 to a stopping point 52, the resistance steadily decreases, which is indicative of PM accumulation. In this active zone 46, according to the disclosed embodiment, the sensor measurement controller 23 determines the total accumulated particulate. The total accumulated PM is measured in the active zone 46 according to the method 64 illustrated in FIG. 10, for example. Between the stopping point 52 (onset of regeneration) and conclusion of deadband (point 50, FIG. 4A) preceded by regeneration (48 in FIG. 4B), no meaningful data can be directly gathered as the resistance measurement during regeneration (as commanded by the sensor measurement controller 23) changes abruptly in the response to soot oxidation and after, for the duration of the deadband zone 44, remains generally unchanged since the sensor experiences an early soot accumulation period dominated by the bias resistor.

The sensor measurement controller 23 is configured to identify an error effect based upon an anomaly relating to the accumulation of the particulate matter. One such anomaly is due to large particle (LP) strikes on the sensor 20. It can be appreciated that once the size of a large particle approaches the width of the electrodes 34, the deposition of this large particle across the electrodes results in a step-like decay of the measured sensor resistance. This step change in resistance is then erroneously interpreted as spikes in soot flux and leads to erroneous interpretation of the measured time elapsed between zone markers (i.e., starting and stopping points 50, 52) representing calibrated sensor resistance thresholds. Thus, in addition to obtaining an inaccurate total accumulated PM, the sensing cycle will be unnecessarily shortened, which results in proportionally more time in the deadband zone 44 and the regeneration zone 48 wherein PM data is not collected. Noticeably, same size large particle strikes result in gradually decreasing step size in the affected sensor resistance trace as time/deposition of soot progresses.

The reason for this non-linearity in the sensor signal response to same size large particle strike lies in the fact that the sensor resistance is the combination of the three resistors 28, 30, 32 connected in parallel, and resistance representing gradually increasing soot deposit.

Conversely, a particle blow-off condition creates another anomaly in which a step-like increase of the measured sensor resistance occurs due to particles becoming dislodged from between the electrodes 34. An additional condition in which a large particle or agglomerate makes intermittent contact with the sensor electrodes 34 is sensed as a blow-off condition that alternates with large particle strikes in a repeated manner is termed an "unstable soot deposit condition." This surface instability where the resistance signal suddenly increases and then decreases again in a repeating pattern is undesirable for PM measurement. The sensor measurement controller 23 initiates a sensor regeneration when the unstable soot deposit condition is detected as no meaningful PM accumulation data can be gathered (cycle abort procedure).

Figure 5:
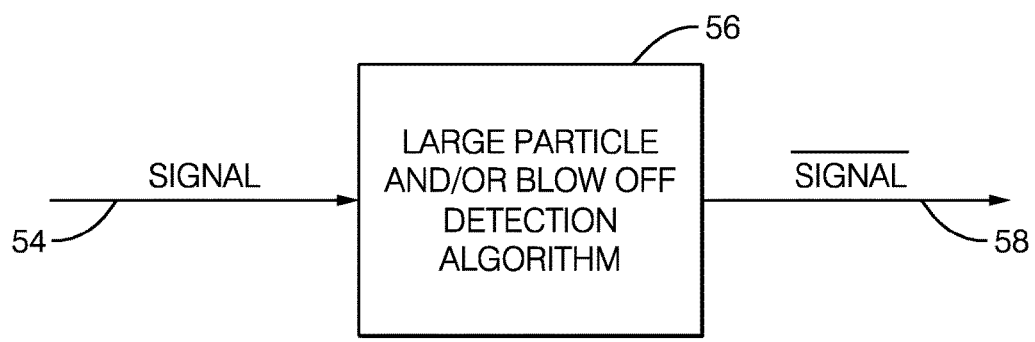
FIG. 5 schematically depicts a signal correction to remove an error effect based upon an anomaly relating to particulate matter accumulation on the sensor.
Figure 9A:
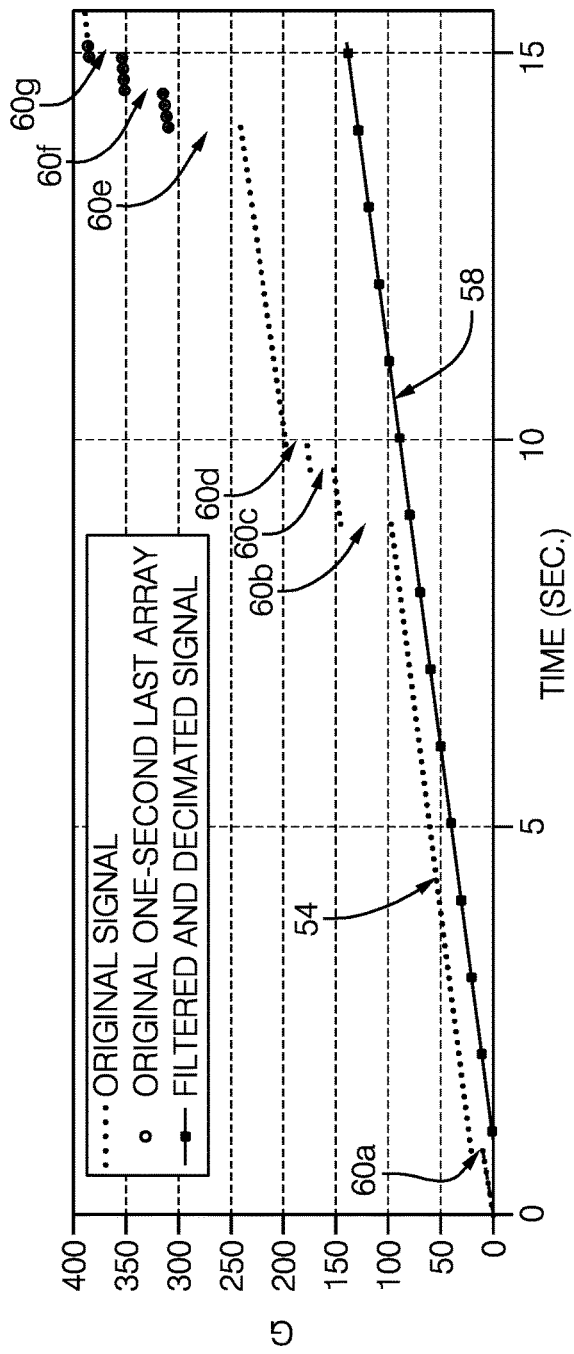
FIG. 9A illustrates a corrupted original conductance signal and a reconstructed conductance signal after conforming erroneous data points, identified by analyzing the first differential of the corrupted conductance signal, which is shown in FIG. 9B.
Figure 9B:
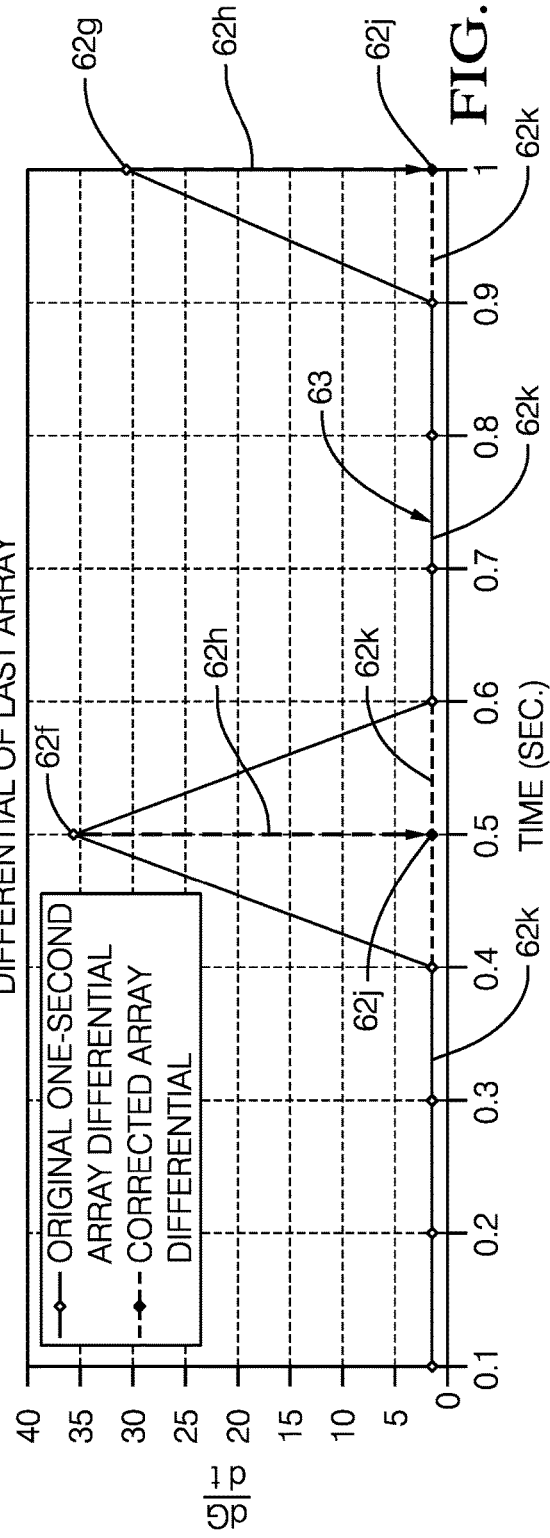
FIG. 9B illustrates the first differential of the corrupted conductance signal with the erroneous data points, and a corrected first differential of the corrupted conductance signal after the erroneous data points have been conformed.

FIG. 5 schematically depicts a signal correction of a corrupted signal 54 to remove the above error effects 56 based upon an anomaly, such as large particle strikes and/or blow-offs that occur during particulate matter accumulation on the sensor. A reconstructed signal 58 is generated with the error effects removed. An example of signal correction is depicted in FIGS. 9A and 9B, for example.

Figure 6A:
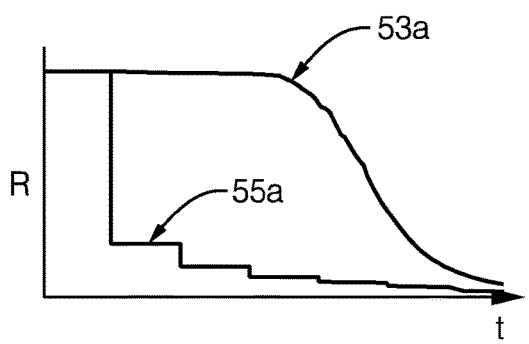
FIG. 6A illustrates a "clean" signal and a "corrupted" signal in resistance versus time.
Figure 7A:
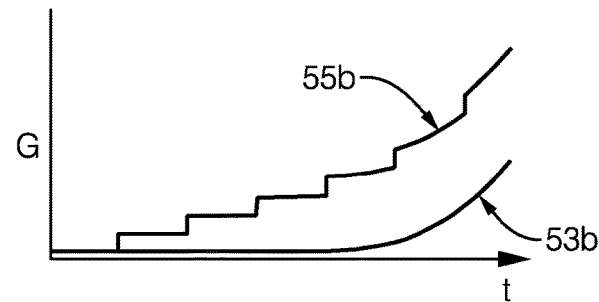
FIG. 7A illustrates a "normal" signal and a "corrupted" signal in conductance versus time for the resistance shown in FIG. 6A.
Figure 6B:
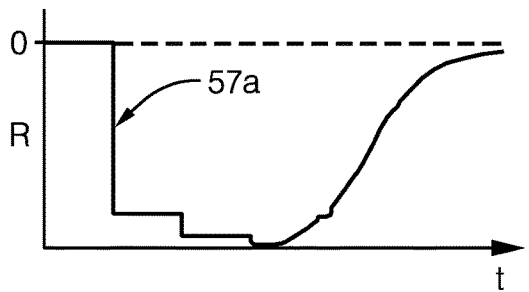
FIG. 6B illustrates the difference between the "normal," i.e., not affected by large particles strikes and/or blow-offs, signal and the "corrupted" signal shown in FIG. 6A.
Figure 7B:
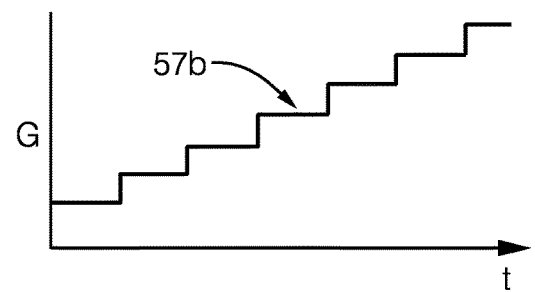
FIG. 7B illustrates the difference between the "normal" conductance signal and the "corrupted" sensor's conductance signal shown in FIG. 7A.

FIG. 6A illustrates a "normal" signal 53a and a large particles strike—"corrupted" signal 55a (i.e. an irregular signal shape) in resistance versus time for an identical, repetitive large particle strike condition. FIG. 6B illustrates the mathematical difference 57a between the "normal" signal and the "corrupted" signal shown in FIG. 6A ("corrupted" minus "normal"), which highlights non-linearity induced by algorithms operating in the electrical resistance domain when processing the PM sensor signal. Thus, the sensor measurement controller 23 is configured to convert the resistance signal to a conductance signal, which provides a signal shape that is much easier to process—even when corrupted. FIG. 7A illustrates a "normal" signal 53b and a "corrupted" signal 55b in the conductance domain versus time, which is generally parabolic in shape with anomalies generated by identical large particle strikes inducing well-behaved step changes. FIG. 7B illustrates the mathematical difference 57b between the "normal" signal and the "corrupted" signal shown in FIG. 7A ("corrupted" minus "normal"), which provides a more manageable, uniform step response to large particle strikes.

Figure 8C:
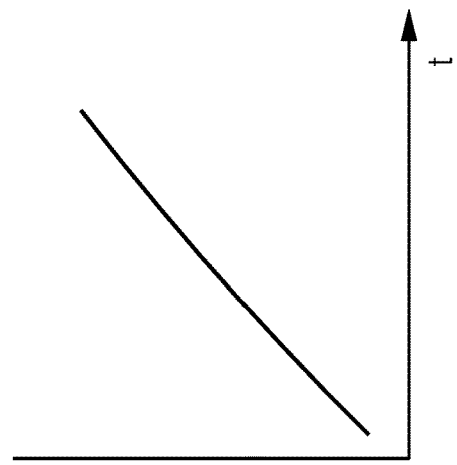
FIGS. 8A, 8B and 8C respectively illustrate a resistance signal, a conductance signal, and a first derivative of the conductance signal in the case of constant soot concentration, constant sensor surface temperature, and constant exhaust gas velocity.
Figure 8B:
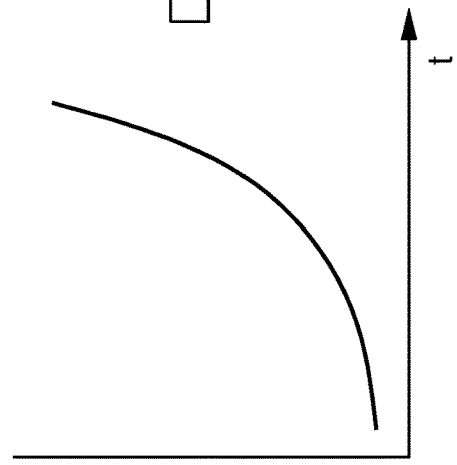
Figure 8A:
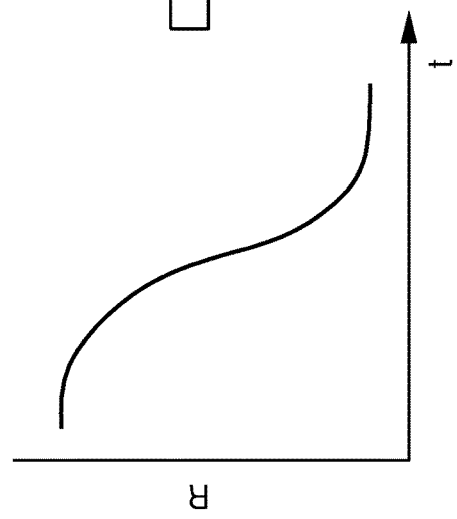

Thus, the disclosed correction method converts the resistance signal (FIG. 8A) to the conductance signal (FIG. 8B), which is a generally parabolic shape for engine steady-state conditions (constant soot flux, constant sensor surface temperature, and constant exhaust velocity). The first differential of the conductance is calculated (FIG. 8C), which provides a generally linear signal. The error effect in the first differential of conductance will manifest itself as erroneous data points that depart from the otherwise generally linear signal. The large particle condition will manifest itself as a sudden, short duration increase in the first differential of the conductance (sudden decrease in resistance signal). Conversely, the blow-off condition will manifest itself as a sudden, short duration decrease in the first differential of the conductance (sudden increase in resistance signal). Once the abnormalities are removed and the conductance signal of the sensor reconstructed without the effect of large particle strikes and/or blow-offs, the integral of the differential conductance is calculated to determine the total accumulated particulate matter, which is used for sensor regeneration and/or engine/vehicle diagnostics and testing procedures.

The sensor measurement controller 23 is configured to determine a total accumulated particulate matter while accounting for the error effect of large particles and/or blow-offs. Referring to FIGS. 9A and 9B, a corrupted signal due to large particle strikes is shown, which results in erroneous data points that are dissimilar to the trend provided by the other data points. A differential of the conductance signal is calculated at a first sampling frequency. Consecutive differentials are compared to identify an erroneous differential in an abnormal signal based upon an anomaly relating to the accumulation of the particulate matter. In the example, the first sampling frequency includes a first sample point from a previous array, and the second sampling frequency includes decimated samples from the corrected array. The erroneous differential in the abnormal signal is reconstructed to produce a corrected, decimated conductance signal at a second sampling frequency that is lower than the first sampling frequency.

In the example, the conductance signal is sampled at, for example, 100 ms intervals (FIG. 9A), and after replacement of conductance differential array elements (FIG. 9B) violating the threshold limits for large particles and blow-offs, the conductance array is reconstructed at a fraction of the original sampling frequency, in the illustrated case at one second intervals (FIG. 9A, squares linked by solid line). Of course, other time intervals can be used, if desired. The data in FIG. 9B is for a small time period and therefore does not reflect the second order curvature that is present in the full cycle data set.

The large particle strikes are indicated by the increases 60a-60g, resulting in a corrupted signal 54. FIG. 9B more closely examines the first differential of the signal at 60f and 60g that respectively correspond to the increases 60f and 60g with anomalies evident in the differential at 62f and 62g respectively. The controller 22 identifies these erroneous data points by sampling the conductance signal at a high rate (in this example 100 ms), creating an array of 11 closely spaced samples, for example. This array is then differentiated, which facilitates identification of anomalies by comparison of adjacent sample amplitudes. The normal operation of the sensor produces a relatively stable differential array with small fluctuations. Large deviations (above a threshold level) are identified anomalies (62f and 62g), which are the subject of correction. The algorithm then modifies the identified points by leveling the differential (62h) to the normal level in that array, resulting in the conformed differentials 62j. The conformed signal (generally straight line 62k in FIG. 9B) is then used for reconstruction of sensor conductance 58 in new sampling domain (in our example 1 second).

For large particle conditions corrected in the manner above, an accurate total accumulated particulate matter of normal size distribution is represented by the corrected conductance trace. The large particle strike condition causes a sudden decrease in the resistance signal (or increase in conductance). However, for large particle conditions, the conformed erroneous data points represent removal of the particle from the ongoing measurement. To maintain overall accuracy, the large particles are accounted for by calculating the effective size of the large particle based on the size of the disturbance and then added to the normal particulate accumulation mass to provide an accurate total accumulated particulate matter.

The formulas for detecting the anomalies may be programmed using the syntax described below. The differential between two subsequent readings is not expected be larger than a certain pre-defined level (called threshold(1)) under normal PM accumulation if compared to the prior measured differential, otherwise the data point is flagged as being a large particle anomaly.

In general, an input array of differential d may have size length(d) which is indicated in the formulation below and is shown as an input array of ten elements in FIG. 9B, which illustrates how the 100 ms sampled conductance differential signal is transformed 62h to reconstruct the error-free (large particles-free) conductance differential 62j and then the decimated conductance signal 58 in FIG. 9A in 1 second sampling domain (correction followed by decimation).

The syntax for large particles detection may look as follows:

```
for m=1:length(d)−1
    if (d(m+1)−d(m))>threshold(1)
        flag1=flag1+1;
        a1=a1+d(m+1)−d(m);
        d(m+1)=d(m);
    end
end
```

This formula provides for correction of excessive differential to the previous one in the array, which relies upon overlapping one of the ten element arrays of signal differentials by one sample from the previous array to allow for correction when the first element in the array violates the threshold. The last element of the previous array is provided only to compare to the first element of new array and "level" (if correction is needed) the first element in the new array with the last element of the previous array. Alternatively, if the desired correction is expected to "level" the output to an average of a few previous readings, then the overlap in the array needs to be adjusted accordingly.

If the correction formula is expanded to more than one element overlap, the sizes of the arrays, number of elements fed back with 1 second delay, and number of elements grounded at the output must be adjusted accordingly.

Similarly, with a different threshold level (threshold(2)) calibration assigned for the detection of blow-offs, the corresponding portion of the syntax embedded into the module may look as follows:

```
for m=1:length(d)−1
    if d(m+1)<−threshold(2)
        flag2=flag2−1;
        a2=a2+d(m+1)−d(m);
        d(m+1)=d(m);
    end
end
```

A particulate blow-off condition on the sensor causes a sudden increase in the resistance signal (or decrease in conductance). The reconstructing step includes increasing the erroneous conductance differential to a level represented by a previous, not questionable or already corrected element, or mean or median of previous elements, in the pre-defined in length array or earlier array if the questionable element is first in a currently processed array.

The subroutines for large particles and blow-off detections follow each other in the algorithm and are executed only if the violation of the relevant threshold level(s) is/are sensed. This action facilitates counting independently the occurrences of large particle (flag1), blow-off (flag2) conditions, and adds up independently the differential amplitudes indicative of large particle and blow-off events (a1 and a2), which provide information on the severity of the misbehavior. Also, when the large particle differential a1 is scaled (calibrated) it provides additional information regarding cumulative mass of the deposit and/or size of the large particles involved. Sizing of the differential a2 can be used to assess severity of the blow-off, thus is useful in the interpretation of the phenomena, but is not used when monitoring total cumulative deposit as the blow-off-corrected conductivity signal inherently nullifies the signal corruption induced by blow-offs. The core output of the filter, however, is an array of corrected conductance signal differentials which is subsequently used to reconstruct the input conductance signal in the new sampling domain of 1 second, for example.

The correction procedure starts at the conclusion of the sensor regeneration 48 and ends at the conclusion of active zone 46 and the onset of next regeneration. The reading of the sensor resistance/conductance, when compared to calibrated maximum conductance marking the upper limit of soot accumulation at the sensor's surface (FIG. 4A, point 52) provides the trigger signal for the sensor regeneration. The reading of the sensor conductance at the onset of the new cycle is represented by the conductance of the clean (not contaminated with soot) substrate in parallel with the bias resistor.

While large particle strikes are expected to be rare, unusual events, it is expected that minute blow-offs occur frequently. If all negative differentials of the conductance were flagged as blow-offs, electronic noise would be misinterpreted as minute blow-off and, therefore, create erroneous corrections. Consequently, the threshold level for blow-offs is set at the level ignoring the system-specific electronic noise. The blow-off threshold level, threshold(2), can be experimentally selected to filter out this "background" effect so that the reconstructing step is performed above the minimum blow-off detection level. Similarly, every particle strike results in a minute increase of the conductance. However, only very large particle strike events require the filter action leading to the correction of the conductance signal. Consequently, the threshold level, threshold(1), which violation initiates the correction for large particle strike is set differently and its value can be roughly estimated using a simulation-based-calibration modeling technique.

Figure 10:
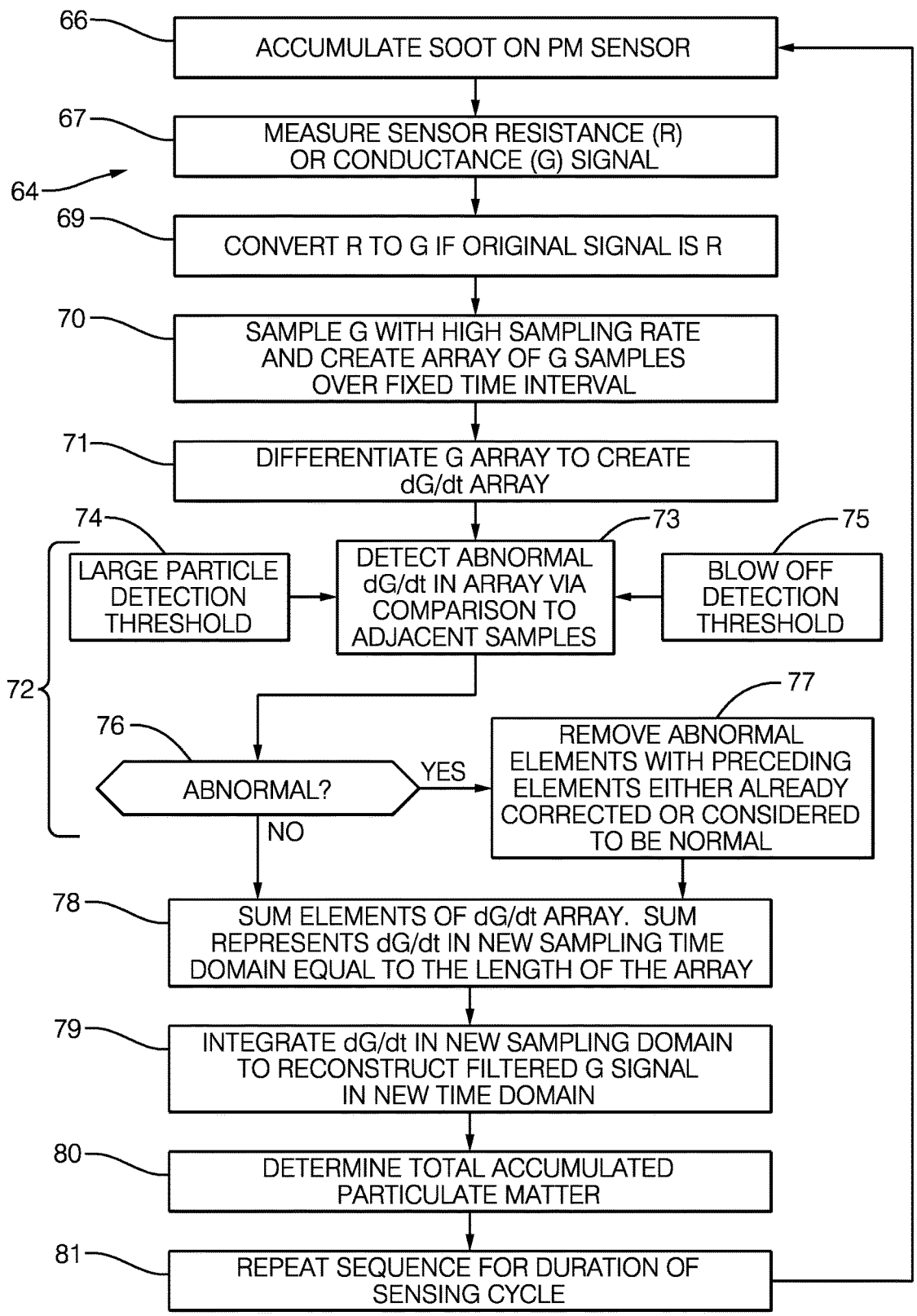
FIG. 10 is a flow chart depicting an example method of correcting a particulate matter sensor signal.

In summary, one example method of PM measurement and correction is illustrated in the flowchart shown in FIG. 10. Soot is accumulated on the PM sensor 20, as indicated at block 66. The amount of PM is output as a resistance signal (and later converted to conductance in block 69), or as a conductance signal, as indicated at block 67. Conductance is sampled at a relatively high rate to create a conductance array over a fixed time interval (block 70), and a first differential array of the conductance is created (block 71).

Anomalies are detected in an abnormal first differential signal of the conductance by making comparisons to adjacent samples, as indicated by block 73. Using large particle strike and blow-off detection thresholds (blocks 74 and 75), undesired deviations from the adjacent samples are identified, and if sufficiently abnormal (block 76), are removed with respect to normal sample points to remove the error effects of the anomaly (block 77). The sample points in the revised array of the first differential of conductance are then summed in a new sampling time domain equal to the length of the array (block 78), and this new sampling time domain can then be reconstructed to provide a filtered conductance signal that is error-free with respect to the anomaly (block 79). The total accumulated PM can then be determined from this corrected conductance signal (block 80). The sequence can be repeated throughout the measurement cycle (block 81) to provide a continuous output of total accumulated PM during engine operation in a vehicle or an engine dynamometer.

There may be a brief period toward the end of the deadband zone 44 during which accumulated PM may be detectable as the effects of the bias resistor 32 are overcome, for example, from about 11 MΩ to about 8 MΩ. Moreover, PM may accumulate during the deadband zone 44 in an unexpected manner, which is indicative of an anomaly such as large particle strikes. For example, the resistance may suddenly drop much earlier than expected such that the effects of the bias resistance are overcome prior to an expected time threshold. For at least these reasons, it also may be desirable to use the disclosed PM measurement and correction during the deadband zone 44.

The controllers 21-24, which may be integrated with one another or separate, may include a processor and non-transitory memory where computer readable code for controlling operation is stored. In terms of hardware architecture, such a controller can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

The controllers may be a hardware device for executing software, particularly software stored in memory. The processor can be a custom made or commercially available processor, a central processing unit (CPU), an auxiliary processor among several processors associated with the controller, a semiconductor based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or nonvolatile memory elements (e.g., ROM, etc.). Moreover, the memory may incorporate electronic, magnetic, optical, and/or other types of storage media. The memory can also have a distributed architecture, where various components are situated remotely from one another, but can be accessed by the controller.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The input/output devices that may be coupled to system I/O Interface(s) may include input devices, for example, but not limited to, a scanner, microphone, camera, proximity device, etc. Further, the input/output devices may also include output devices, for example but not limited to a display, etc. Finally, the input/output devices may further include devices that communicate both as inputs and outputs, for instance but not limited to, a modulator/demodulator (for accessing another device, system, or network), a radio frequency (RF) or other transceiver, a bridge, a router, etc.

When the controller is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

It should be understood that although particular step sequences are shown, described, and claimed, the steps may be performed in any order, separated or combined unless otherwise indicated and will still benefit from the present invention.

Although the different examples have specific components shown in the illustrations, embodiments of this invention are not limited to those particular combinations. It is possible to use some of the components or features from one of the examples in combination with features or components from another one of the examples.

Furthermore, although an example embodiment has been disclosed, a worker of ordinary skill in this art would recognize that certain modifications would come within the scope of the claims. For that reason, the following claims should be studied to determine their true scope and content.

What is claimed is:

1. A method of estimating particulate matter in an exhaust stream comprising the steps of:
   accumulating a particulate matter on a sensor, wherein the sensor provides a signal that varies based upon an amount of the particulate matter on the sensor;
   calculating a differential of a conductance signal related to the signal;
   comparing consecutive differentials to identify an erroneous differential in an abnormal signal based upon an anomaly relating to the accumulation of the particulate matter; and
   reconstructing the abnormal signal by correcting the erroneous differential to produce a corrected, decimated conductance signal.

2. The method according to claim 1, wherein the signal is an electrical resistance signal with the anomaly and has an irregular signal shape, and the conductance signal has a generally parabolic shape with the anomalies inducing well-behaved step changes.

3. The method according to claim 2, wherein the calculating step includes generating a first differential signal from the conductance signal to provide a generally linear signal.

4. The method according to claim 3, wherein the calculating step is performed at a first sampling frequency, and the reconstructing step is performed at a second sampling frequency that is lower than the first sampling frequency.

5. The method according to claim 4, wherein the reconstructing step includes conforming the erroneous differential to the generally linear signal, which provides a decimated conductance signal that is generally linear.

6. The method according to claim 5, comprising a step of determining a total accumulated particulate matter adjusted for the anomaly, wherein the anomaly corresponds to a large particle strike condition on the sensor, the large particle strike condition causing a sudden increase in the conductance signal, the reconstructing step includes decreasing the erroneous differential to a level represented by a previous, not questionable or already corrected element, or mean or median of previous elements in the measurement sample array, or earlier array if the questionable sample is the first element in a currently processed array.

7. The method according to claim 6, wherein the total accumulated particulate matter determining step is performed subsequent to the reconstructing step and includes adding in a compensation for the erroneous differential created by large particles, thus retaining the fidelity of the determining step by including the mass of the large particle.

8. The method according to claim 5, comprising a step of determining a total accumulated particulate matter adjusted for the anomaly, wherein the anomaly corresponds to a particulate blow-off condition on the sensor causing a sudden decrease in the conductance signal, the reconstructing step includes increasing the erroneous differential to a level represented by a previous, not questionable or already corrected element, or mean or median of previous elements in the measurement sample array, or earlier array if the questionable sample is the first element in a currently processed array.

9. The method according to claim 8, comprising a step of defining a system-specific electronic noise representing a minimum blow-off detection level which would cause rejection of noise-driven conductance signal and an undesired differential correction, wherein the reconstructing step is performed above the minimum blow-off detection level.

10. The method according to claim 4, wherein individual arrays of the first sampling frequency include a first sample point which represents the last sampling point from a previous array, and the second sampling frequency includes decimated samples from a corrected array.

11. The method according to claim 10, wherein the first sampling frequency is multiple times the second sampling frequency.

12. The method according to claim 1, comprising a step of performing a measurement cycle that includes a deadband zone, followed by an active zone, which is followed by a regeneration zone, wherein the accumulating, calculating, comparing and reconstructing steps are performed during the active zone.

13. The method according to claim 12, comprising an exhaust system fluidly connected to an engine, the exhaust system defines the exhaust stream, the sensor includes a heater and is provided in the exhaust system, and comprising the step of energizing the heater in the regeneration zone.

14. The method according to claim 13, comprising a step of initiating a regeneration of the sensor once the total accumulated particulate matter reaches a predetermined threshold based on the corrected conductance signal.

15. The method according to claim 13, comprising a step of initiating a regeneration of the sensor prior to the total accumulated particulate matter reaching a predetermined threshold if an unstable soot deposit condition is identified.

16. The method according to claim 15, wherein the anomaly corresponds to the unstable soot deposit condition on the sensor, the unstable condition corresponding to sudden increases and decreases in the conductance signal in a repeating pattern.

17. A system comprising:
   an exhaust system fluidly configured to define an exhaust stream;
   a sensor arranged in the exhaust system and configured to be exposed to the exhaust stream and accumulate a particulate matter on the sensor, wherein the sensor provides a signal that varies based upon an amount of the particulate matter on the sensor; and a control system in communication with sensor, control system includes a controller configured to calculate a differential of a conductance signal related to the signal, compare consecutive differentials to identify an erroneous differential in an abnormal signal based upon an anomaly relating to the accumulation of the particulate matter, and reconstruct the abnormal signal by correcting the erroneous differential to produce a corrected, decimated conductance signal, wherein the control system is configured to determine a total accumulated particulate matter adjusted for the anomaly.

18. The system according to claim 17, wherein the sensor includes a heater, and the controller is configured to energize the heater based upon the total accumulated particulate matter.

19. The system according to claim 17, wherein the control system performs a sensing cycle that includes a deadband zone, followed by an active zone, which is followed by a regeneration zone, wherein the controller is configured determine the total accumulated particulate matter during the active zone.

20. The system according to claim 19, wherein the control system outputs particulate matter data continuously during vehicle operation or during an engine test procedure.

\* \* \* \* \*